United States Patent
Kietzmann

(10) Patent No.: US 6,851,784 B1
(45) Date of Patent: Feb. 8, 2005

(54) METHOD AND DEVICE FOR RECORDING AN IMAGE ON DROP-PRODUCING DISPENSING HEADS

(75) Inventor: Markus Kietzmann, Wolfratshausen (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 0 days.

(21) Appl. No.: 09/581,103
(22) PCT Filed: Dec. 8, 1998
(86) PCT No.: PCT/EP98/07952

§ 371 (c)(1),
(2), (4) Date: Aug. 29, 2000

(87) PCT Pub. No.: WO99/30169

PCT Pub. Date: Jun. 17, 1999

(30) Foreign Application Priority Data

Dec. 8, 1997 (DE) .......................... 197 54 459

(51) Int. Cl.⁷ ............................................. B41J 29/393
(52) U.S. Cl. .......................... 347/19; 250/573; 356/337
(58) Field of Search .................... 347/19, 23; 250/573; 356/337–340

(56) References Cited

U.S. PATENT DOCUMENTS

| 5,601,980 A | 2/1997 | Gordon et al. ................. 435/6 |
| 5,621,524 A * | 4/1997 | Mitani ........................ 356/338 |

FOREIGN PATENT DOCUMENTS

| DE | 43 08 082 A1 | 9/1994 | |
| EP | 0 364 203 A1 | 10/1989 | |
| EP | 0 641 599 | 6/2000 | |
| GB | 2 259 568 A | 7/1991 | |
| JP | 404027552 A * | 1/1992 | ................. 347/19 |
| WO | WO 97/44134 | 11/1997 | |

* cited by examiner

*Primary Examiner*—Thinh Nguyen
*Assistant Examiner*—Julian D. Huffman
(74) *Attorney, Agent, or Firm*—Cook, Alex, McFarron, Manzo, Cummings & Mehler, Ltd.

(57) ABSTRACT

In an image-recording system (10) for a dispensing head (50) with numerous dispensers (51, 52, 53, . . . ), in which a predetermined light path from a lighting device (20) to an image-recording device (40) intersects a drop release area of a drop-releasing dispenser (52), a deviating device (30) is provided with which a measuring light segment (33) is formed along a predetermined reference line through the drop release area, wherein the lighting and image-recording devices (20, 40) are spaced apart from the reference line.

10 Claims, 2 Drawing Sheets

METHOD AND DEVICE FOR RECORDING AN IMAGE ON DROP-PRODUCING DISPENSING HEADS

FIELD OF THE INVENTION AND RELATED ART

The invention relates to a device and a procedure for recording drop or particle images on a dispenser head, in particular for stroboscopic image recording of microdrops during formation on a dispenser tip or after release from the latter.

A dispensing head consists of numerous electrically actuatable dispensers (e.g., electrically actuatable micropipettes), which are each set up to release a microdrop in response to an electric trigger signal. To this end, each dispenser has a trigger device that generates a pressure pulse whose parameters depend on the duration and amplitude of the trigger signal.

One important application for dispensing heads lies in the area of biotechnology, genetic engineering or chemical technology, where the goal is to initiate a combined reaction between the smallest quantities of working substances in the form of microdrops on substrates. To ensure that the reaction proceeds efficiently, it is necessary that the microdrops (volumes in the sub-microliter range) be positioned precisely on the reaction substrate with a reproducible drop size and speed. Therefore, there is interest in systems for analyzing and evaluating the drop separation from the dispenser, the direction of drop movement, the drop size and, if necessary, the drop number.

The principle of such a generally known system is shown in FIG. 4 (prior art). An image-recording device 1 consists of a stroboscope lamp 2 and a camera 4. The camera 4 is equipped with a lens (normally a microscope lens) focused on a drop release area located in front of the micropipette tip 5. Extending from the stroboscope lamp 2 to the camera 4 is a light path that crosses the drop release area, so that the camera 4 can record a drop T during separation or in flight. Such an image-recording device is generally provided as a fixed laboratory system to which the dispensing head is moved in such a way that the micropipette tip projects into the light path. The actual expansions of the camera 4 and stroboscope lamp 2 are shown by example with dashed lines. To precisely observe the drops, it is necessary that drop formation take place under constant lighting and image-recording conditions. However, when using multi-channel dispensing heads with numerous planar dispensers, this results in the following problem.

If the dispensers of a multi-channel dispensing head are distributed over a surface whose characteristic expansion is greater than the focal depth of the lens system in the camera 4, an obstruction arises between the dispensing head and the camera setup when positioning a dispenser to be observed in the focal point of the lens, extending into the traveling path of the dispenser (see arrow). The same applies with respect to lighting, since the distance from the stroboscope lamp to the drop must remain as constant as possible. Since the focal depth of the lens system normally ranges from 10 mm to 30 mm, this problem is already encountered at low dispenser numbers on a dispensing head given a dispenser distance of 9 mm, for example. The conventional system fails completely in the case of dispenser heads wherein dispensers are arranged in matrixes of 4*4 or 8*12 dispenser rows.

WO 97/44134 discloses devices and a procedure for monitoring the microdrop release from pulsed microdrop firing devices. The microdrop release is controlled using a piezoelectric converter. The drop release from microdispensers is also described in the publication by A. V. Lemmo et al. in "Anal. Chem.", Ed. 69, 1997, pp. 543 forward.

SUMMARY OF THE INVENTION

The object of the invention is to indicate an improved device for recording drop images, which makes it possible to record an image on multi-channel dispenser heads under conditions that remain constant for all dispensers. The object of the invention is also to indicate a procedure for using such an image-recording device.

This object is solved by devices and a procedure described in claims herein. Advantageous embodiments of the invention are described in the subclaims.

The invention provides a new image-recording arrangement in which a deviating device modifies the light path from a lighting device to an image-recording device that passes through a drop release area of a drop-releasing dispenser to be observed. The deviating device is provided to guide the light path from the lighting device to the image-recording device over a measuring light segment that is located at a sufficient perpendicular distance from the lighting and image-recording devices, and in which each dispenser of a dispensing head can be freely positioned. The deviating device consists of at least two reflector elements (mirrors) that fix the measuring light segment. The measuring light segment runs perpendicular to the longitudinal expansion of the dispenser to be measured, and passes by the tip of the respective dispenser, so that a drop can be optically detected immediately after released from the dispenser. Therefore, the reflector elements are designed in such a way that they partially project into the distance between adjacent dispensers of a dispensing head. The reflector elements are arranged in such a way that the light path from the lighting device to the image-recording device runs over the measuring light segment in one plane. The reflector elements form a distance in which the dispenser to be measured can traverse, wherein the drop is released along a straight path running parallel to the measuring light plane.

In a preferred configuration, the lighting and image-recording devices are arranged in a reference plane (e.g., laboratory table plane or the like), which has a perpendicular distance from a reference line formed by the measuring light segment with respect to the longitudinal expansion of the dispensers or drop releasing device. The lighting and image-recording devices include all optical components that provide the measuring light in an area lying under the surface fixed by the dispensers of the dispensing head during image recording in the measuring position.

The subject of the invention is also a procedure for analyzing drop parameters, in which a dispensing head is positioned over an image-recording system with lighting and image recording devices and a deviating device in such a way that a dispenser to be observed projects into a measuring light segment formed by the deviating device at a distance from the lighting and image-recording devices.

The advantage to the invention is that an image can be recorded for drop analyses on dispenser heads of any size for all dispensers under constant optical conditions. The deviating device of the image-recording system according to the invention makes it possible to freely position the dispensing head relative to the image recording system. The image recording system has a simple structure, and permits a simple correction of any arising image distortions after image recording using an image processor.

Additional details and advantages of the invention will be described below making reference to the attached drawings, which show:

DETAILED DESCRIPTION OF THE PREFERRED EMBODIMENT

In the following, the invention will be described making reference to a dispenser row, but can also be advantageously used in the same way during the drop analysis of individual dispensers or planar dispenser groups arranged in matrixes. The invention is not limited to the described stroboscope technique, but can rather be realized with any other image-recording technique that responds quickly enough.

Figure 1:
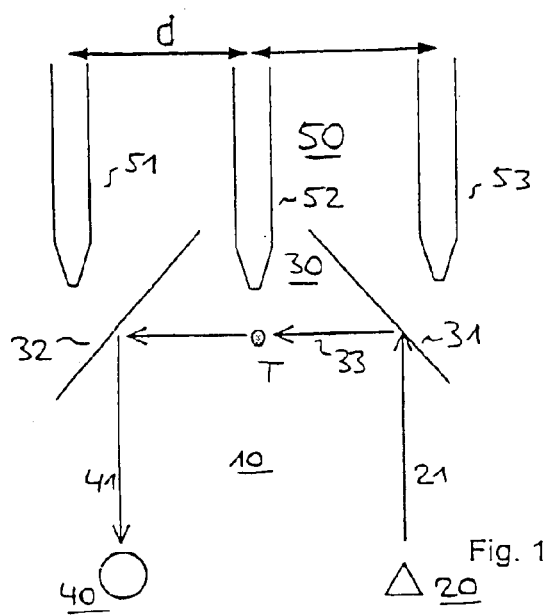
FIG. 1 a first embodiment of an image-recording system according to the invention, FIG. 2 a second embodiment of an image-recording system according to the invention, FIG. 3 a third embodiment of an image-recording system according to the invention, and FIG. 4 a conventional image-recording system (prior art).

In FIG. 1, an image-recording system 10 encompasses a lighting device 20, a deviating device 30 and an image-recording device 40. The expansion of individual components (e.g., see FIG. 3) is not separately indicated for reasons of clarity. The lighting device 20 contains a stroboscope lamp, e.g., formed by a pulsed, light-emitting diode (LED). The LED is preferably operated at an overvoltage exceeding the normal operating voltage to achieve as high a luminance as possible during pulse operation. The lighting device can also consist of another stroboscope lamp, e.g., in the form of a suitably expanded and pulsed laser. The image-recording device 40 preferably consists of a CCD camera with a microscope lens having a focal depth ranging from 10 mm to 30 mm. However, other detector systems with any cameras (even one-dimensional in the form of a CCD line, if necessary) and normal or macro lenses are possible, whose structure is adapted to the parameter of the drop to be detected.

A lighting light path 21 leads from the lighting device 20 to the deviating device 30, which fixes a measuring light segment 33 that is adjoined by the image-recording light path 41 to the image-recording device 40. The measuring light segment 33 leads through the drop release area through which passes a drop T released from the dispenser 52 to be observed. The measuring light segment 33 leading through the drop release area extends along a reference line lying in a plane directly adjacent to the surface fixed by the dispenser tips of the dispensing head. While retaining a predetermined lighting distance from the lighting device 20 to the drop T or a predetermined focal distance from the drop T to the image-recording device 40, the deviating device 30 formed by the flat mirrors 31, 32 now makes it possible to position the lighting and image-recording devices at a sufficient distance from the plane in which the reference line lies, or to position them with a sufficient perpendicular distance from the reference line, so that the lighting and image-recording devices do not impede movement of the dispensing head parallel to the mentioned plane.

The mirrors 31, 32 are inclined relative to the measuring light segment 33 by predetermined deviating angles (e.g., 45°), and the middles of the mirrors are spaced apart by a distance corresponding to distance d of the dispensers 51, 52, 53, . . . of the dispensing head 50. The edges of mirrors 31, 32 to be pointed toward one another are spaced apart, so that a dispenser to be observed can project between the mirrors 31, 32. As a result, the mirrors of the deviating arrangement 30 limit the drop release area of the dispenser. The drops are released in the plane fixed by light paths 21, 33, 41.

Figure 2:
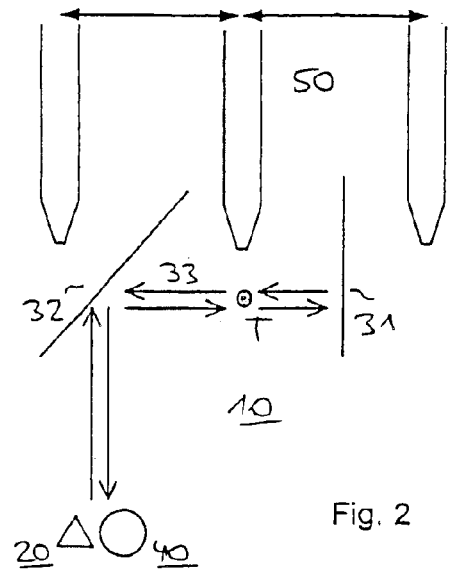

In the alternative configuration shown in FIG. 2, the deviating device 30 comprises a mirror 32 inclined relative to the measuring light segment 33, and a mirror 31 sitting perpendicular on the latter. In this case, the lighting light path 21 is identical to the image-recording light path 41. The lighting and image-recording devices 20, 40 are provided with an inclined beam splitter (not shown). As in the embodiment shown in FIG. 1, the lighting and image-recording devices 20, 40 are spaced apart from the reference plane in which the measuring light segment 33 runs.

In the system according to FIG. 2, the deviating mirror 31 situated parallel on the measuring light segment 33 can be omitted. In this case, the shadow of the backlit drop is not recorded as in FIG. 1, but rather the frontlit image of the drop. In another modification, it is also possible to separate the lighting light path 21 from the image recording light path 41, and allocate the lighting device 20 to a suitable position at a distance from the dispensing head 50. In this case, the deviating device 30 only consist of a flat mirror 32, since the drop recorded with front lighting itself acts as a reflector. Correspondingly, the measuring light segment 33 extends from the drop T to the deviating mirror 32.

Figure 3:
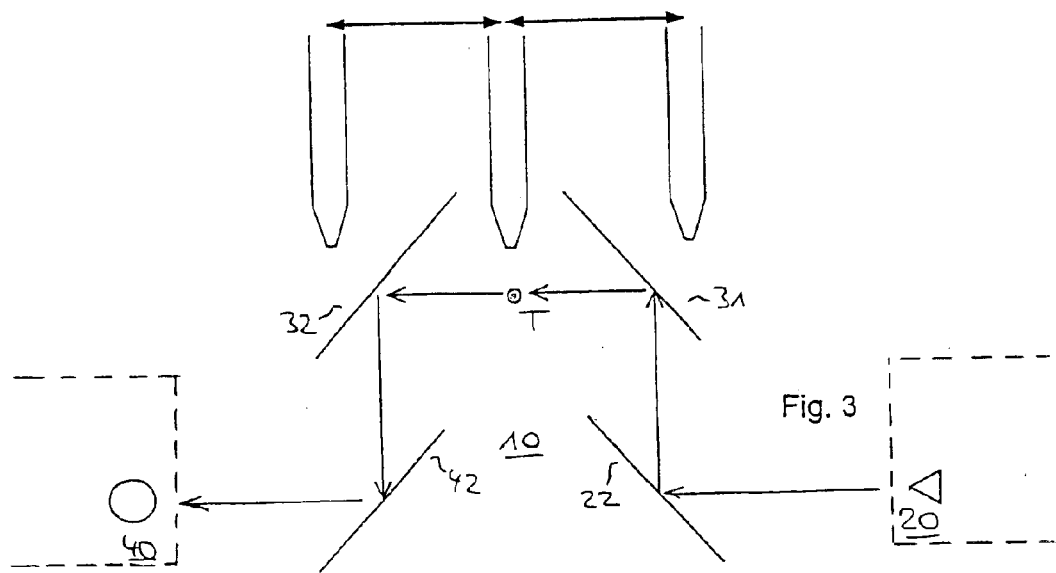
Figure 4:
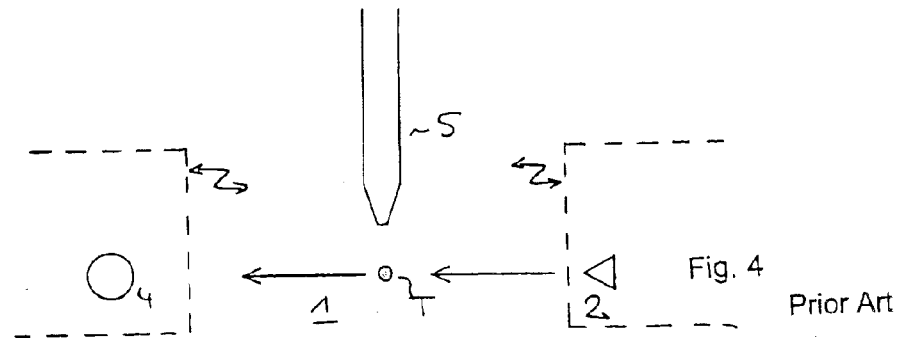

FIG. 3 shows another configuration of the invention. The lighting and image-recording devices 20, 40 interact with the deviating mirrors 22, 42. The deviating device 30 otherwise corresponds to the structure according to FIG. 1. The structure according to FIG. 3 is advantageously compatible with conventional image-recording systems (see FIG. 4). The lighting and image-recording devices 20, 40 are arranged on a shared, flat carrier (e.g., laboratory table). The straight light path between both devices is interrupted by the mirror combination 31, 32, 22, 42.

Partial light paths are formed, which in particular incorporate the measuring light segment 33 at a distance from the carrier plane. The traveling plane of the dispenser is spaced far enough away from the physical expansions of the lighting and image-recording devices marked with dashed lines.

To analyze the drop, a dispensing head is positioned in such a way relative to the image-recording system that the measuring light segment passes through the drop release area of a relevant dispenser. When using micropipettes for the above applications, the drop release area can exhibit a characteristic size of roughly 5 mm under the dispensing tip. The length of the measuring segment then measures roughly 10 mm. The diameters of the drops to be detected measure roughly 10 $\mu$l to 100 $\mu$m. A reference image is first recorded with the dispenser at the measuring position. While recording the reference image, stroboscope flashes of the drop-free light path are taken. For example 10 stroboscope flashes (length roughly 3 $\mu$s) are recorded and stored in an image processing system (not shown). The drop image is then recorded, a process which involves recording images of all phases of drop formation, release and movement for a complete drop analysis. To this end, the dispenser releases a sequence of drops, wherein a delay time between the respective trigger signal of the electrically actuated dispenser and a trigger signal of the stroboscope lighting device is variably set for each drop. Depending on the parameters of the release signal, the delay time can measure up to 500 $\mu$s. The sequence of drop images with varying delay times corresponding to the different phases of drop formation is stored and subjected to digitization and image processing that essentially involves working out the difference using the reference images. This compensates for any noise introduced through the mirrors of the deviating device, and any luminescence profile present at the LED of the lighting device. It is possible to record a group of drop images (e.g., 10) under constant recording conditions (in particular a constant delay time) for each drop formation phase, and accumulate the individual images to improve image quality. The operating frequency of the image-recording device (e.g., image readout frequency to a CCD camera) is then preferably adjusted to the drop frequency in such a way that the drop frequency corresponds to an integer multiple of the operating frequency (e.g., $f_{drop}$=100 Hz, $f_{camera}$=50 Hz).

This is followed by an analysis of the corrected drop images with respect to the drop size (drop volume, working substance amount) and movement properties of the drop. The movement properties include the direction of drop movement and drop speed. If the direction of drop movement does not coincide with the dispenser alignment (e.g., vertical alignment perpendicular to measuring light segment), the dispenser is corrected, or the dispenser tip where solid particles of a working substance might have been deposited is cleaned. The speed is measured by evaluating two drop images of released drops with varying delay times. The drop speed is calculated from the difference in delay times and the corresponding position change. Additional results of the image analysis include the detection of satellite drops or omitted drops, if the dispenser becomes clogged or the release pressure in the dispenser is too low. In addition, it is possible, and in certain applications necessary, to optimize the amplitude and duration of the trigger signal of the dispenser to desired parameters or for quality control by observing the drop properties.

After the parameters of a dispenser have been analyzed, all dispensers of a dispensing head are sequentially moved to the measuring light segment. The mentioned measuring process is then executed for each of the dispensers.

The position of the dispensing head preferably leaves the length of the lighting light path and image recording light path unchanged, so that the drop-generating processes on each of the dispensers can be recorded under identical optical conditions and with a high accuracy and reproducibility.

What is claimed is:

1. An image-recording system for a dispensing head with numerous dispensers, in which a predetermined light path from a lighting device to an image-recording device intersects a drop release area of a drop-releasing dispenser to be detected, characterized in that a deviating device is provided with which a measuring light segment is formed along a predetermined reference line through said drop release area, and that said lighting and image-recording devices are spaced apart from the said reference line relative to said drop releasing dispenser, in which said deviating device has first and second mirrors, said second mirror inclined by a first deviating angle relative to said reference line, said first mirror deflects light from said lighting device into said measuring light segment, and said second mirror deflects light from said measuring light segment to said image-recording device.

2. The image-recording system according to claim 1, in which said first and second mirrors project into the gaps between said drop-releasing dispenser to be detected and said adjacent dispensers.

3. The image-recording system according to claim 1, in which a third mirror that deflects light from said lighting device to said first mirror is provided, along with a fourth mirror that deflects light from said second mirror to said image-recording device.

4. The image-recording system according to claim 1, in which said lighting device consists of a pulsed light emitted, and said image-recording device has a camera with a lens.

5. A measuring system for recording images of drops on a drop-releasing dispenser to be detected with numerous dispensers of a dispensing head having an image-recording system according to claim 1, in which said lighting and image-recording devices are arranged in a carrier plane over which said dispensing head can traverse, so that the tips of said dispensers move in a reference plane parallel to said carrier plane, wherein said deviating device forms said measuring segment at a perpendicular distance from said carrier plane and directly adjacent to said reference plane.

6. The measuring system according to claim 5, in which the length of said measuring light segment is essentially identical to the distance (d) of adjacent dispensers of said dispensing head.

7. A method for recording images of drops on a drop-releasing dispenser of a dispensing head using an image-recording system according to claim 1, in which said dispensing head is positioned relative to said image-recording system in such a way that said dispenser projects towards said measuring light segment.

8. The method according to claim 7, in which images are recorded by detecting a sequence of drops with varying delay times between a trigger signal of said dispenser and a trigger signal of said lighting device operated as a stroboscope.

9. The method according to claim 8, in which said image recording is preceded by a reference image recording with a drop-free measuring segment, and differential images are generated from said recorded drop images and the reference images for image processing.

10. The method according to claim 7, in which image recording is preceded by a reference image recording with a drop-free measuring segment, and differential images are generated from said recorded drop images and the reference images for image processing.

* * * * *